(12) United States Patent
Kramer et al.

(10) Patent No.: US 10,882,800 B2
(45) Date of Patent: Jan. 5, 2021

(54) INTEGRATED GASIFICATION AND ELECTROLYSIS PROCESS

(71) Applicant: Gas Technology Institute, Des Plaines, IL (US)

(72) Inventors: Andrew Kramer, St. Charles, IL (US); James Seaba, Barrington, IL (US); David Lamont, Palatine, IL (US)

(73) Assignee: Gas Technology Institute, Des Plaines, IL (US)

( * ) Notice: Subject to any disclaimer, the term of this patent is extended or adjusted under 35 U.S.C. 154(b) by 0 days.

(21) Appl. No.: 16/405,262

(22) Filed: May 7, 2019

(65) Prior Publication Data

US 2020/0017422 A1 Jan. 16, 2020

Related U.S. Application Data

(60) Provisional application No. 62/697,540, filed on Jul. 13, 2018.

(51) Int. Cl.
*C07C 1/04* (2006.01)
*C07C 1/12* (2006.01)
*C10J 3/72* (2006.01)
*C10J 3/84* (2006.01)
(Continued)

(52) U.S. Cl.
CPC ............. *C07C 1/0485* (2013.01); *C07C 1/12* (2013.01); *C10J 3/72* (2013.01); *C10J 3/84* (2013.01); *C10K 3/06* (2013.01); *C10L 3/08* (2013.01); *C10J 2300/093* (2013.01); *C10J 2300/0916* (2013.01); *C10J 2300/1603* (2013.01); *C10J 2300/1625* (2013.01);
(Continued)

(58) Field of Classification Search
CPC .. C01B 3/34; C01B 3/24; C01B 3/047; C10L 3/08; C10L 2290/04; C10L 2290/02; C10L 2290/06; C10L 2290/36; C10L 2290/38; C10L 2290/42; C10L 2200/0469; C10J 3/721; C10J 2300/0976; C10J 2300/0959; C10J 2300/094; C07C 1/12; C25B 1/04; Y02E 60/366; Y02E 60/364
See application file for complete search history.

(56) References Cited

U.S. PATENT DOCUMENTS

2015/0284651 A1* 10/2015 Stuermer .................. C10L 3/08
518/716
2016/0115405 A1 4/2016 Zubrin et al.
2018/0171250 A1 6/2018 Chapman et al.

OTHER PUBLICATIONS

M. Gassner et al., "Thermo-economic optimisation of the integration of electrolysis in synthetic natural gas production from wood", Energy 33, pp. 189-198 (2008).

* cited by examiner

*Primary Examiner* — Jafar F Parsa
(74) *Attorney, Agent, or Firm* — Banner & Witcoff, Ltd.

(57) ABSTRACT

Aspects of the invention relate to improvements in the flexibility with which oxygen and hydrogen, for example from electrolysis, may be supplied to processes having both gasification and methanation steps, as well as improvements in how such processes may be operated in response to variations in carbonaceous feeds. Offsets, between the ideal quantity of hydrogen and the quantity available from a given source may be compensated for by adjusting one or more operations of the process, and in particular such operation(s) that ultimately impact the quantity of CO and/or $CO_2$ available downstream of the gasifier for conversion to methane in an RNG product stream.

27 Claims, 2 Drawing Sheets

(51) Int. Cl.
*C10K 3/06* (2006.01)
*C10L 3/08* (2006.01)
(52) U.S. Cl.
CPC ............... *C10J 2300/1662* (2013.01); *C10L 2200/0469* (2013.01); *C10L 2290/04* (2013.01)

INTEGRATED GASIFICATION AND ELECTROLYSIS PROCESS

CROSS-REFERENCE TO RELATED APPLICATIONS

This application claims priority to U.S. provisional application No. 62/697,540, filed Jul. 13, 2018, which is incorporated by reference in its entirety.

FIELD OF THE INVENTION

Aspects of the invention relate to gasification processes for the production of renewable natural gas (RNG), with such processes being integrated with electrolysis for supplying oxygen and hydrogen feeds.

DESCRIPTION OF RELATED ART

The gasification of coal has been performed industrially for over a century in the production of synthesis gas that can be further processed into transportation fuels. More recent objectives of developing energy independence with reduced greenhouse gas emissions has led to a strong interest in using biomass as a gasification feed, and thereby a potential source of renewable natural gas (RNG). According to a multi-step process, biomass gasification is performed first, by partial oxidation in the presence of an oxidant gas containing oxygen and other possible components such as steam. Gasification at elevated temperature and pressure, optionally in the presence of a catalytic material, produces an effluent with methane and oxides of carbon (CO, $CO_2$), as well as hydrogen. This effluent, which may be referred to as syngas in view of its CO and $H_2$ content, is normally treated to remove a number of undesired components such as particulates, alkali metals, sulfur compounds, and tars (generally referring to organic compounds having a boiling point temperature greater than that of benzene). Such treatment steps render the gasifier effluent suitable for downstream conversion of the high concentrations of $H_2$ and $CO/CO_2$ by catalytic methanation, in order to increase the methane content in a resulting RNG stream.

As may be appreciated from the atomic composition of wood and other forms of biomass, the gasifier effluent generally lacks sufficient hydrogen for complete conversion of the feed carbon content to methane, resulting in an excess of CO and $CO_2$ that must be considered in the overall process economics. The addition of hydrogen to allow more complete utilization of biomass carbon in producing methane is therefore of considerable interest. Hydrogen is often available as a product obtained from steam reforming of methane and/or other hydrocarbons, according to a technology that is very robust but suffers from the significant amount of energy required. In addition, the use of fossil methane to produce such hydrogen defeats the purpose of obtaining natural gas from purely renewable sources. The integration of hydrogen from electrolysis, as a potential source to allow more complete methanation of gasifier effluents, has been proposed by Gassner et al. (ENERGY 33 (2008): 189-198) and Dace et al. (ENERGY PROCEDIA 75 (2015): 801-806). Further developments in biomass gasification, to improve economics relative to fossil-derived natural gas production, are nonetheless needed to realize its commercial scale implementation in the production of RNG.

SUMMARY OF THE INVENTION

Aspects of the invention are associated with the discovery of gasification processes for the production of methane, having improved efficiencies in the management of feeds input to, and/or energy derived from, such processes. Providing electrolysis oxygen and hydrogen to such processes can advantageously reduce the overall carbon footprint associated with the production of RNG from a carbonaceous feed such as coal or biomass. For example, electrolysis oxygen can be used to augment the quantity supplied to a gasifier from a conventional air separation unit (ASU), whereas the co-generated electrolysis hydrogen can be provided to a methanation reactor and thereby improve the utilization of carbon in the feed for methane production. This, in turn, creates further opportunities for integration, particularly in terms of the additional heat generation from the exothermic methanation reaction that can be recovered in the form of steam and ultimately electricity to power the electrolyzer.

Particular aspects relate to improvements in the flexibility with which electrolyzer oxygen and hydrogen may be supplied to processes having both gasification and methanation steps, as well as improvements in how such processes may be operated in response to variations in carbonaceous feeds. In this regard, a typical ASU is associated with high capital and operating costs, and its capacity may often be misaligned with the need for pure oxygen in the gasifier. This can occur, for example, if an ASU is unavailable in a proper size to be economical and/or supplemental sources of oxygen such as pressure swing adsorption (PSA) cannot provide sufficient purity. Both ASU and PSA are recognized for their potential to generate oxygen, but they also produce nitrogen that is not always readily utilized or monetized. Whereas hydrogen may be available from conventional reforming, this production method is energy intensive and is normally based on fossil-derived hydrocarbons. Electrolysis therefore has the potential to address a number of shortcomings associated with the production of purified oxygen and/or hydrogen by other methods, in addition to offering improvements in overall feed carbon utilization (e.g., methane yield) and heat integration.

The quantity of electrolysis oxygen, whether or not supplied in combination with other sources such as ASU oxygen or PSA oxygen, may be determined primarily or entirely by the quantity and type of carbonaceous feed to the gasifier. However, the corresponding amount of electrolysis hydrogen produced, in satisfying this oxygen demand, is generally not optimal for complete conversion of CO and $CO_2$, generated by gasification, in the downstream methanation reactor. Advantageously, such offsets, between the ideal quantity of hydrogen and the quantity available as the stoichiometric amount obtained from water electrolysis to satisfy the oxygen demand of the gasifier, may be compensated for by adjusting one or more operations of the process, and in particular such operation(s) that ultimately impact the quantity of CO and/or $CO_2$ available downstream of the gasifier for conversion to methane in an RNG product stream. Such operation to be adjusted may alternatively, or additionally, impact the $CO/H_2$ molar ratio and/or the $CO_2/H_2$ molar ratio downstream of the gasifier. Otherwise, if sufficient electrolysis hydrogen is available, representative processes comprising gasification and methanation may exclude such operation(s) altogether, thereby simplifying RNG production and reducing the associated costs.

Embodiments of the invention are directed to processes for producing methane, for example as an RNG product, with such processes comprising both gasification and methanation. Gasification refers to the contacting of a carbonaceous feed, in a gasifier (or, more particularly, a gasification reactor of a gasifier), with an oxygen-containing gasifier feed, to provide a gasifier effluent comprising CO, $CO_2$, $H_2$, and/or $H_2O$, and generally all of these components. At a point upstream of a methanation reactor, or otherwise within the methanation reactor, electrolysis hydrogen obtained from an electrolyzer may be combined with the gasifier effluent. The added, or makeup, electrolysis hydrogen, or at least a portion thereof, is reacted in the methanation reactor with at least a portion of the CO and/or $CO_2$ in the gasifier effluent to form methane and thereby improve the utilization of carbon in the carbonaceous feed, in the production of RNG. Advantageously, an operation of the process, for example one or more of a series of operations performed on the gasifier effluent downstream of the gasifier and upstream of the methanation reactor, may be adjusted in response to the makeup quantity or flow rate of the electrolysis hydrogen, to improve overall process efficiency. The operation that is adjusted is namely one that affects the concentration of CO and/or $CO_2$ in the feed to the methanation reactor, with representative operations being a sour shift operation or an acid gas removal operation. The operation that is adjusted may alternatively, or additionally, be one that affects the $CO/H_2$ molar ratio and/or the $CO_2/H_2$ molar ratio of the feed to the methanation reactor.

Other embodiments of the invention are directed to integrated gasification, methanation, and electrolysis processes for producing RNG. Representative processes comprise contacting, in a gasifier of a gasification zone, biomass with an oxygen-containing gasifier feed to provide a gasification zone effluent comprising CO, $CO_2$, $H_2$, and/or $H_2O$, and generally all of these components. The oxygen-containing gasifier feed comprises electrolysis oxygen obtained from electrolysis of water in an electrolyzer. The processes further comprise converting, in a methanation reactor of a methanation zone, at least a portion of the CO and/or the $CO_2$ in the gasification zone effluent to methane. The RNG is obtained as, or the RNG is recovered from (e.g., following one or more optional purification steps), a methanation zone effluent. The gasification zone or the methanation zone, or both, comprise at least one operation affecting the CO concentration or the $CO_2$ concentration, or causing a change in such concentration from the feed to that operation to the product of that operation. Alternatively, or in combination, the gasification zone or the methanation zone, or both, comprise at least one operation affecting the $CO/H_2$ molar ratio and/or the $CO_2/H_2$ molar ratio, or causing a change in such molar ratio from the feed to that operation to the product of that operation. The processes may yet further comprise adjusting the at least one operation in response to a makeup quantity or flow rate of electrolysis hydrogen. This makeup quantity may be the entire flow rate of electrolysis hydrogen added to the process in one or more locations between the gasifier and the methanation reactor (e.g., added to either the gasification zone or the methanation zone, or both), with some or all of this makeup quantity being reacted to form methane in the methanation reactor. This makeup quantity of electrolysis hydrogen may be a substantially stoichiometric amount, or substantially twice the molar flow rate of electrolysis oxygen added to the gasifier in the oxygen-containing gasifier feed, which may comprise one or more separate gaseous feed streams.

The gasification zone and/or methanation zone may comprise one or more operations as described herein, which may or may not affect, or may at least substantially affect, the methanation reactor feed or inlet CO concentration or $CO_2$ concentration. Alternatively, or in combination, the gasification zone and/or methanation zone may comprise one or more operations as described herein, which may or may not affect, or may at least substantially affect, the methanation reactor feed or inlet $CO/H_2$ molar ratio and/or $CO_2/H_2$ molar ratio. The gasification zone may be separated from the methanation zone by a compression stage.

Yet other embodiments of the invention are directed to processes for producing methane, with such processes comprising gasifying a carbonaceous feed to provide a gasifier effluent comprising CO, $CO_2$, $H_2$, and/or $H_2O$, and generally all of these components. The processes also comprise introducing a makeup quantity of hydrogen to the methanation reactor or upstream of the methanation reactor, to react at least a portion of the makeup hydrogen with at least a portion of the CO and/or $CO_2$ in the gasifier effluent to form methane. Such processes may further comprise adjusting an operation of the process in response to the makeup quantity of hydrogen. Advantageously, representative processes may exclude at least one processing step that would otherwise affect the methanation reactor feed, or methanation reactor inlet, CO concentration or $CO_2$ concentration. Alternatively, or in combination, such processes may exclude at least one processing step that would otherwise affect the methanation reactor feed, or methanation reactor inlet, $CO/H_2$ molar ratio and/or $CO_2/H_2$ molar ratio. This impact on concentration or molar ratio may be caused by consuming or producing CO and/or $CO_2$, by reaction in the operation (and therefore in the overall process), for example in the case of a sour shift operation. The excluded processing step(s) may be that/those which would otherwise affect the methanation reactor feed, or methanation reactor inlet, CO concentration or $CO_2$ concentration, by adding CO and/or $CO_2$ to, or removing CO and/or $CO_2$ from, the operation (and therefore the overall process), for example in the case of an acid gas removal operation. The excluded processing step(s) may be that/those which would otherwise alternatively affect, or which would otherwise additionally affect, the methanation reactor feed, or methanation reactor inlet, $CO/H_2$ molar ratio and/or $CO_2/H_2$ molar ratio, by such addition and/or removal of CO and/or $CO_2$, to and/or from the operation (and therefore the overall process).

These and other embodiments, aspects, and advantages relating to the present invention are apparent from the following Detailed Description.

BRIEF DESCRIPTION OF THE DRAWINGS

A more complete understanding of the exemplary embodiments of the present invention and the advantages thereof may be acquired by referring to the following description in consideration of the accompanying figures, in which the same reference numbers are used to identify the same features.

Figure 1:
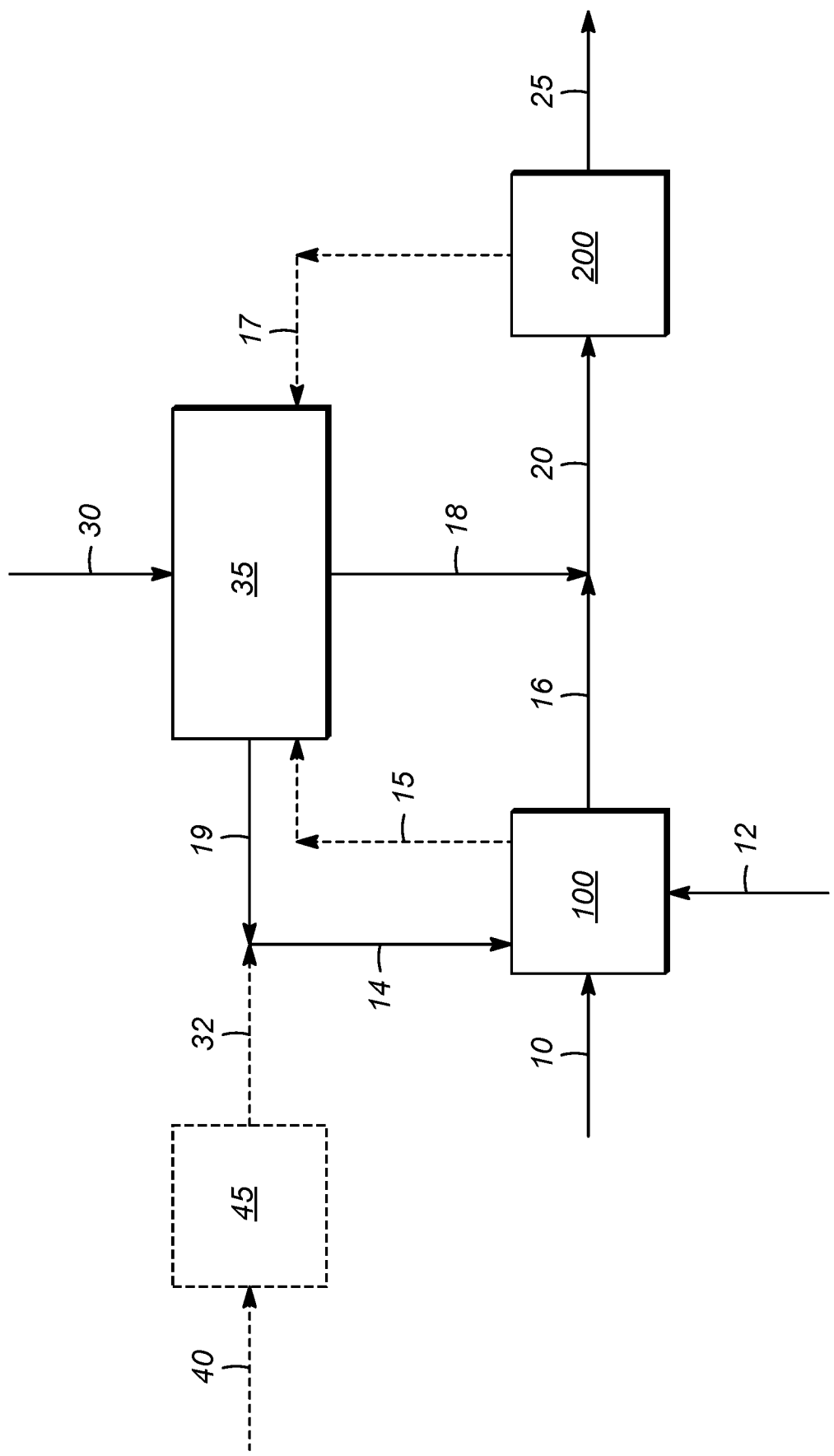
FIG. 1 depicts a flowscheme illustrating generally the integration of an electrolyzer with a gasification zone and a methanation zone to produce methane according to representative processes described herein.
Figure 2:
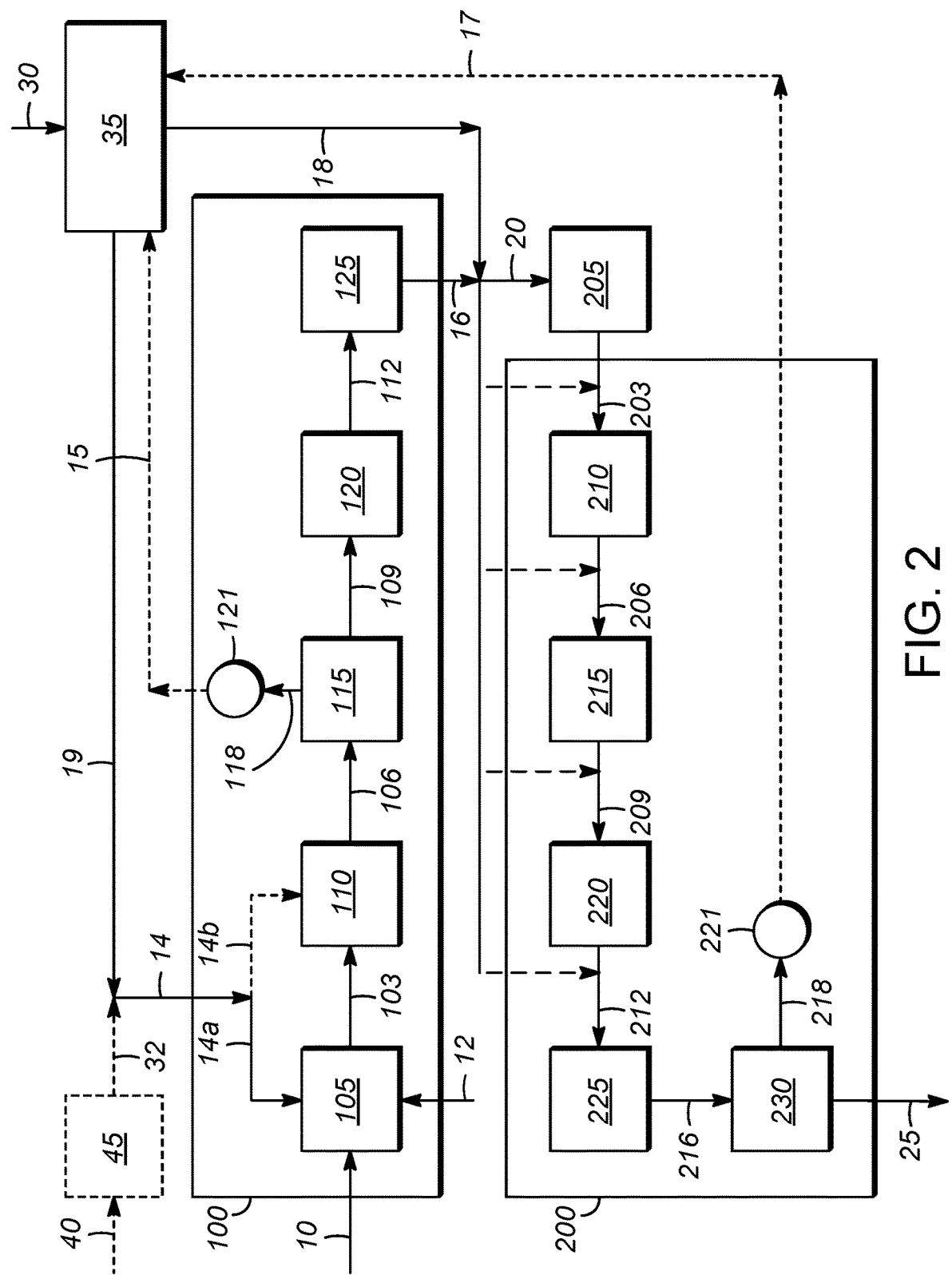
FIG. 2 depicts a flowscheme illustrating particular operations within the gasification zone and methanation zone that may be carried out in process illustrated in FIG. 1.

The same numbers are used between FIGS. 1 and 2 to designate the same or similar elements. In order to facilitate explanation and understanding, these figures provide a simplified overview. Associated equipment such as vessels, heat exchangers, valves, instrumentation, and utilities, is not shown, as its specific description is not essential to the implementation or understanding of the various aspects of the invention. Such equipment would be readily apparent to those skilled in the art, having knowledge of the present disclosure. Other processes for producing methane according to other embodiments within the scope of the invention, having configurations and constituents determined, in part, according to particular processing objectives, would likewise be apparent.

DETAILED DESCRIPTION

The expressions "wt-%" and "mol-%," are used herein to designate weight percentages and molar percentages, respectively. The expressions "wt-ppm" and "mol-ppm" designate weight and molar parts per million, respectively. For ideal gases, "mol-%" and "mol-ppm" are equal to percentages by volume and parts per million by volume, respectively.

Embodiments of the invention are directed to a process for producing methane from a carbonaceous feed by gasification and methanation, performed in a gasifier and methanation reactor, respectively, in which a source of makeup hydrogen is added to the process to improve the overall utilization of carbon in the carbonaceous feed in producing methane (i.e., to improve methane yield, based on the feed carbon content). If the source of makeup hydrogen is obtained from the electrolysis of water, then advantageously this reactant, as opposed to hydrogen generated from the steam reforming of fossil hydrocarbons, is a carbon-free resource that does not contribute to the carbon footprint associated with the methane that is produced. According to some embodiments, therefore, the methane may be produced predominantly, if not entirely, from renewable feeds, including biomass as the carbonaceous feed, air and/or electrolysis oxygen, and electrolysis hydrogen. Moreover, some or all of the electrical energy needed for the electrolysis may be obtained as heat recovered from the gasifier or exothermic methanation reactor.

In a gasifier (or, more particularly, a gasification reactor of a gasifier), the carbonaceous feed is subjected to partial oxidation in the presence of an oxygen-containing gasifier feed in an amount that this generally limited to supply only 20-70% of the oxygen that would be necessary for complete combustion. The oxygen-containing gasifier feed may also comprise other oxygenated gaseous components including $H_2O$ and/or $CO_2$. A gasifier effluent is produced, comprising CO, $CO_2$, and methane ($CH_4$) that are derived from the carbon present in the carbonaceous feed, as well as $H_2$ and/or $H_2O$, and generally both, together with other components in minor concentrations. The carbonaceous feed may comprise coal (e.g., high quality anthracite or bituminous coal, or lesser quality subbituminous, lignite, or peat), petroleum coke, asphaltene, and/or liquid petroleum residue, or other fossil-derived substance. In a preferred embodiment, the carbonaceous feed may comprise biomass. The term "biomass" refers to renewable (non-fossil-derived) substances derived from organisms living above the earth's surface or within the earth's oceans, rivers, and/or lakes. Representative biomass can include any plant material, or mixture of plant materials, such as a hardwood (e.g., whitewood), a softwood, a hardwood or softwood bark, lignin, algae, and/or *lemna* (sea weeds). Energy crops, or otherwise agricultural residues (e.g., logging residues) or other types of plant wastes or plant-derived wastes, may also be used as plant materials. Specific exemplary plant materials include corn fiber, corn stover, and sugar cane bagasse, in addition to "on-purpose" energy crops such as switchgrass, *miscanthus*, and algae. Short rotation forestry products, such as energy crops, include alder, ash, southern beech, birch, *eucalyptus*, poplar, willow, paper mulberry, Australian Blackwood, sycamore, and varieties of *paulownia* elongate. Other examples of suitable biomass include vegetable oils, carbohydrates (e.g., sugars), organic waste materials, such as waste paper, construction, demolition wastes, digester sludge, and biosludge. Representative carbonaceous feeds therefore include, or comprise, any of these types of biomass. Particular carbonaceous feeds comprising biomass include municipal solid waste (MSW) or products derived from MSW, such as refuse derived fuel (RDF). Carbonaceous feeds may comprise a combination of fossil-derived and renewable substances, including those described above.

Downstream of the gasifier, a methane product may be obtained from an effluent of the methanation reactor directly, or otherwise recovered from this effluent following additional purification and/or treatment. Carbon utilization to produce methane, and consequently methane yield, in the overall process are improved by virtue of adding the makeup hydrogen (e.g., improved relative to a baseline process in which the makeup hydrogen is absent). For example, carbon utilization and/or methane yield (e.g., based on carbon present in biomass or other carbonaceous feed) may be increased by at least about 3%, at least about 5%, or at least about 10%, relative to a baseline process in which no makeup hydrogen (e.g., electrolysis hydrogen) is added. For comparative purposes, such baseline process may have all gasifier, or gasification zone, parameters maintained the same, while the methanation reactor, or methanation zone, is operated to maximize methane yield according to the baseline process.

Importantly, processes as described herein may be operated to address constraints associated with the use of electrolysis hydrogen and oxygen, in which the electrolysis oxygen requirement may be governed all or predominantly by the amount and type of carbonaceous feed to be gasified, whereas the corresponding amount of electrolysis hydrogen generated may be sub-optimal for converting all CO and $CO_2$ obtained from the gasifier to methane. In this case, one or more operations of the process, which affect the CO and/or $CO_2$ concentrations of the methanation reactor inlet, may be adjusted or controlled (e.g., by continuous feedback) to reduce waste and enhance overall process economics. The one or more operations to be adjusted may alternatively or additionally affect the $CO/H_2$ and/or $CO_2/H_2$ molar ratios of the methanation reactor inlet.

In some embodiments, this adjustment or control can advantageously be used to maintain complete or substantially complete conversion of CO and/or $CO_2$ in the methanation reactor (or methanation zone), such that a high quality methane product may be obtained directly or recovered, for example, with properties understood in the art to render it of "pipeline quality." A representative methane product, or RNG product in the case of being derived from a renewable carbonaceous feed such as biomass, may have any one, or any combination, of (i) a methane concentration of at least about 90 mol-% (e.g., from about 90 mol-% to about 99 mol-%), or at least about 95 mol-% (e.g., from about 95 mol-% to about 98 mol-%), (ii) a concentration of hydrocarbons other than methane (e.g., a total concentration of $C_2$-$C_6$ hydrocarbons) of less than about 5 mol-%, or less than about 3 mol-%, (iii) a hydrogen concentration of less than about 0.05 mol-%, or less than about 0.01 mol-%, (iv) a $CO_2$ concentration of less than about 2 mol-%, or less than about 1 mol-%, and/or (v) a sulfur concentration of less than about 10 mol-ppm, or less than about 5 mol-ppm. Other properties of the methane product, or RNG product, rendering it suitable for pipeline transport include having a heating value within 5% of that of pure methane and being free of water and toxic or corrosive contaminants. In some embodiments, this product may have a hydrogen concentration of up to about 4 mol-% (e.g., from about 1 mol-% to about 4 mol-%) and nonetheless be considered pipeline quality. Generally, the CO concentration of this product is less than about 1 mol-%, such as less than about 0.1 mol-%.

Representative operations, which may be adjusted by virtue of their impact on the amount(s) and/or concentration(s) of CO and/or $CO_2$ at the inlet of the methanation reactor (e.g., in the total methanation reactor feed or gas entering this reactor), or otherwise by virtue of their impact on the $CO/H_2$ and/or $CO_2/H_2$ molar ratios at the inlet of the methanation reactor, include operations that (i) produce or consume CO and/or $CO_2$ in the process (e.g., generate or produce CO and/or $CO_2$ in the process by reaction, or otherwise react CO and/or $CO_2$ and thereby deplete or consume one or both of these components from the process), or (ii) add and/or remove CO or $CO_2$ in the process (e.g., introduce an additional source of CO and/or $CO_2$, or feed comprising CO and/or $CO_2$, to the process or otherwise separate a stream comprising one or both of these components from the process). Such operations may cause a change (an increase or a decrease) in the absolute concentration, or alternatively the relative amount, of CO and/or $CO_2$ from the inlet of the operation to the outlet of the operation (excluding any flow bypassing the operation) of generally at least about 2% (e.g., from about 2% to about 30%), typically at least about 5% (e.g., from about 5% to about 35%), and often at least about 10% (e.g., from about 10% to about 30%). More particularly, such operation(s) may be adjusted in response to a makeup quantity or flow rate of hydrogen (e.g., electrolysis hydrogen), at least a portion of which is, in turn, reacted in the methanation reactor.

Therefore, in the case of an operation that produces or otherwise adds CO and/or $CO_2$, that operation may be enhanced, or increased, at relatively high quantities of makeup hydrogen and diminished, or decreased, at relatively low quantities of makeup hydrogen. Conversely, in the case of an operation that consumes or otherwise removes CO and/or $CO_2$, that operation may be diminished, or decreased, at relatively high quantities of makeup hydrogen and enhanced, or increased, at relatively low quantities of makeup hydrogen. The ability to regulate, i.e., enhance or diminish, one or more operations that affect (i) the concentration, or overall amount, of CO and/or $CO_2$ at the methanation reactor inlet and/or (ii) the $CO/H_2$ and/or $CO_2/H_2$ molar ratio at the methanation reactor inlet, constitutes an important aspect of the present invention, in terms of improving carbon utilization of biomass or other carbonaceous feed.

An enhancement, or increase, in an operation may involve increasing its capacity, for example by increasing the flow of a solvent or extraction agent for contacting with the feed to that operation, or otherwise increasing a quantity of solid bed material such as an adsorbent or catalyst available for such contacting (e.g., by commissioning an additional vessel containing such material). An enhancement may alternatively involve increasing the severity of the operation, for example by increasing operating temperature and/or pressure, and/or otherwise increasing residence time (e.g., decreasing space velocity). Conversely, a diminishment, or decrease, in an operation may involve decreasing its capacity, for example by decreasing the flow of a solvent or extraction agent for contacting with the feed to that operation, or otherwise decreasing a quantity of solid bed material such as an adsorbent or catalyst available for such contacting (e.g., by decommissioning a vessel containing such material). A diminishment may alternatively involve decreasing the severity of the operation, for example by decreasing operating temperature and/or pressure, or otherwise decreasing residence time (e.g., increasing space velocity). A given operation may also be enhanced or diminished according to an adjustment in which all, or at least a portion, of the feed to the operation is diverted from, for example bypassed around, the operation. In the case of bypass, the bypassed feed to the operation then simply becomes part of a feed to a downstream operation, such as the next successive operation normally performed in the process. In the case of a complete bypass of all of the feed to a given operation, the process essentially operates without that operation, or excludes that operation.

In the case of an operation that produces or otherwise adds CO and/or $CO_2$, an enhancement or increase would directionally produce or add more CO and/or $CO_2$. In the case of an operation that consumes or otherwise removes CO and/or $CO_2$, an enhancement or increase would directionally consume or remove more CO and/or $CO_2$. Conversely, in the case of an operation that produces or otherwise adds CO and/or $CO_2$, a diminishment or decrease would directionally produce or add less CO and/or $CO_2$. In the case of an operation that consumes or otherwise removes CO and/or $CO_2$, a diminishment or decrease would directionally consume or remove less CO and/or $CO_2$.

Having knowledge of the present disclosure, those skilled in the art will readily appreciate the full scope of adjustments that can be performed to a given operation to enhance or diminish its performance, as needed, on the basis of the quantity of hydrogen (e.g., electrolysis hydrogen) being added to the process.

Particular aspects of the invention also relate to process control, whereby one or more operations of the process that affect the concentration, or overall amount, of CO and/or $CO_2$ at the methanation reactor inlet, and/or that affect the $CO/H_2$ and/or $CO_2/H_2$ molar ratio at the methanation reactor inlet, may be adjusted in response to changes in the makeup quantity or flow rate of hydrogen. For example, the control may be such that a given composition of the methanation reactor inlet should be maintained as a set point, with that composition allowing for a high utilization of CO and/or $CO_2$ in the conversion to methane. A set point composition, may, for example, be based on the concentration of $H_2$ in the methanation reactor feed or inlet, relative to the concentrations of CO and/or $CO_2$. A particular set point may be the concentration ratio (or molar ratio) according to $[H_2]/(3\cdot[CO])$, or according to $[H_2]/(3\cdot[CO]+4\cdot[CO_2])$, in which the brackets are used to designate component concentrations. The control may be such that this ratio, and/or some other measure relating to the efficiency with which CO and/or $CO_2$ are utilized, is maintained at a value of 1 or nearly 1, for example generally within the range of about 0.7 to about 1.5, typically within the range of about 0.8 to about 1.3, and often within the range from about 0.9 to about 1.1. In response to a deviation from this ratio, or other measure, from its set point, an operation affecting the concentration, or overall amount, of CO and/or $CO_2$ at the methanation reactor inlet as described herein may be automatically or manually adjusted.

For example, in response to a deviation from the set point that is indicative of an excess concentration of hydrogen (e.g., due to an increased amount or flow rate of makeup hydrogen), an operation that produces or otherwise adds CO and/or $CO_2$, may be enhanced or increased, or an operation that consumes or otherwise removes CO and/or $CO_2$, may be diminished or decreased. Conversely, in response to a deviation from the set point that is indicative of a deficient concentration of hydrogen (e.g., due to a decreased amount or flow rate of makeup hydrogen), an operation that produces or otherwise adds CO and/or $CO_2$, may be diminished or decreased, or an operation that consumes or otherwise removes CO and/or $CO_2$, may be enhanced or increased. Adjustments to enhance or diminish an operation may be according to any of those particularly described herein, with the extent of such enhancement or diminishment possibly being controlled automatically or manually (e.g., the extent of diverting a feed from, for example by bypassing the feed around, an operation may be automatically or manually adjusted, in response to deviations from a set point relating to the efficiency with which CO and/or $CO_2$ are utilized in the methanation reactor.)

A particular operation affecting the methanation reactor inlet CO and/or $CO_2$ concentration is a sour shift operation, which refers to an operation that performs a catalytic water-gas shift (WGS) reaction in the presence of sulfur compounds. Therefore, a sulfur-tolerant WGS catalyst is used in a WGS reactor of this operation. The sour shift operation is used to produce hydrogen by the WGS reaction, according to: $CO+H_2O \rightarrow CO_2+H_2$. Therefore, the sour shift operation, or any WGS operation that may be used in the process generally, downstream of the gasifier and upstream of the methanation reactor, is an operation that consumes CO and produces both $CO_2$ and $H_2$. For purposes of characterizing a sour shift operation, or WGS operation in general, according to the types of operations described above, this may be considered "an operation that consumes or otherwise removes CO and/or $CO_2$," as this operation, if adjusted, would normally be diminished or decreased in response to excess hydrogen and enhanced or increased in response to deficient hydrogen, due to the co-production of $H_2$ by the WGS reaction. In the case of a reverse WGS operation, whether performed in the presence or absence of sulfur compounds, this may conversely be considered "an operation that produces or otherwise adds CO and/or $CO_2$." Another particular operation affecting the methanation reactor inlet CO and/or $CO_2$ concentration is an acid gas removal operation that is "an operation that consumes or otherwise removes CO and/or $CO_2$," since $CO_2$ is removed in this operation, whereas the amount of CO from the feed to the product is generally unaffected. Yet another particular operation that may be considered "an operation that produces or otherwise adds CO and/or $CO_2$," is the gasifier, as this operation, if adjusted, would normally be enhanced or increased in response to excess hydrogen and diminished or decreased in response to deficient hydrogen. Whereas this operation co-produces $H_2$ as a result of gasification reactions, this component is generally produced at less than the stoichiometric ratio with respect to CO, according to the methanation reaction. In a particular example of adjusting the gasifier operation, such that this operation is diminished, or decreased, at relatively low quantities of makeup hydrogen (e.g., in response to a deviation from a set point that is indicative of a deficient concentration of hydrogen) a feed may be diverted from the gasifier. Such feed may be the oxygen-containing gasifier feed, comprising all or a portion of the oxygen (e.g., contained in a makeup quantity of oxygen) that is fed to the process, with such oxygen comprising electrolysis oxygen and/or oxygen separated from air.

With respect to any of the specific WGS (e.g., sour shift), reverse WGS, acid gas removal, or gasifier operations, or generally any other operation of the process that affects (i) the concentration, or overall amount, of CO and/or $CO_2$ at the methanation reactor inlet, and/or (ii) the $CO/H_2$ and/or $CO_2/H_2$ molar ratio at the methanation reactor inlet, such operation may be conveniently adjusted by diverting a feed from, for example by bypassing at least a portion of the feed around, that operation (e.g., using manual or automatic control) as described above. In the case of a sufficient makeup quantity or flow rate of hydrogen (e.g., electrolysis hydrogen), it may be expedient diminish any operation that consumes or otherwise removes CO and/or $CO_2$, to the point at which such operation is not used at all. For example, the sour shift operation and/or the acid gas removal may be bypassed completely in the case of achieving a desired utilization of carbon in the carbonaceous feed. Accordingly, embodiments of the invention are directed to processes as described herein for the gasification of a carbonaceous feed (e.g., biomass), followed by methanation, in which a source of makeup hydrogen is added to the process and the process excludes one or both of a sour shift operation or an acid gas removal operation, such that, for example, the process involves, upstream of the methanation reactor (i) no substantial adjustment of the amount of CO and/or $CO_2$ in the gasifier effluent, and/or (ii) no substantial adjustment of the $CO/H_2$ and/or $CO_2/H_2$ molar ratio in the gasifier effluent. That is, the relative amount of CO and/or $CO_2$ in the gasifier effluent may be changed (e.g., the number of moles of either of these components may be increased or decreased) by less than about 10%, less than about 5%, or even less than about 2%, by virtue of the absence of any operation that substantially produces, adds, consumes, and/or removes CO and/or $CO_2$, and more particularly in the absence of any operation that substantially consumes and/or removes CO and/or $CO_2$. Alternatively, or additionally, the relative $CO/H_2$ molar ratio and/or the relative $CO_2/H_2$ molar ratio may be changed by these percentage ranges. In this manner, advantageously, substantially all CO and/or $CO_2$ produced in the gasifier can be fed to, and preferably utilized in, the methanation reactor for the production of the methane product (e.g., RNG).

Representative operations that may be adjusted in response to a makeup quantity of hydrogen can exclude those operations primarily used to remove components other than CO and/or $CO_2$, but which may nonetheless result in some minimal change in the amount and/or concentration of CO and/or $CO_2$ from the inlet of (or the feed input to) the operation to the outlet of (or the product removed from) the operation. Such operations that may be excluded, i.e., not adjusted as described herein, encompass those used for the removal of tar, solid particles, and sulfur, with particular operations being a tar conversion operation, a gas filtration/scrubbing operation, a supplemental cleaning operation, and a sulfur removal operation, as discussed in greater detail below. Any of these operations, whether considered to reside in a gasification zone or a downstream methanation zone, may be performed on an effluent of the gasifier, prior to its introduction to a methanation reactor.

FIG. 1 illustrates generally the integration of an electrolyzer 35 with a gasification zone 100 and a methanation zone 200, for the production of methane. This methane is namely present in a methanation reactor effluent 25 from methanation zone 200, and is produced from carbon in a carbonaceous feed 10 that is fed to a gasifier of gasification zone 100. Also fed to this zone is a makeup quantity of oxygen 14 that may be obtained entirely as electrolysis oxygen 19 or may otherwise be provided as a combination of electrolysis oxygen 19 and optional air separation unit (ASU) oxygen 32, obtained from the separation of makeup air 40 in ASU 45. ASU 45 can include any technology for separating pure or substantially pure oxygen, such as to obtain, for example, ASU oxygen 32 and/or makeup quantity of oxygen 14 having an oxygen concentration of at least about 90 mol-%, and preferably at least about 95 mol-%. ASU may therefore include, or comprise, pressure swing adsorption (PSA) or vacuum pressure swing adsorption (VPSA), membrane separation, and/or molten salt-based oxygen separation. The use of ASU 45 for removing inert nitrogen from makeup air 40 may be beneficial in terms of reducing equipment sizes, including the gasifier and equipment associated with downstream processing operations, as well as improving the heating value of the gasifier effluent and downstream products, with exemplary downstream operations and products as described herein.

Makeup quantity of oxygen 14 may be determined at least partly (e.g., predominantly or even entirely) on the basis of a makeup quantity of carbonaceous feed 10. According to some embodiments, makeup quantity of oxygen 14 may be determined on the basis of both the makeup quantity and type of carbonaceous feed, particularly if significant changes in characteristics of carbonaceous feed 10 (e.g., its carbon content) occur over the course of a given operation. For example, the makeup quantity of oxygen may be the amount needed for a given degree of oxidation of carbon present in carbonaceous feed, such as a percentage of the stoichiometric oxygen requirement for oxidation to $CO_2$. In representative embodiments, the makeup quantity of oxygen, for example, may be generally from about 20% to about 95%, typically from about 30% to about 90%, and often from about 40% to about 80%, of this stoichiometric requirement.

As is more clearly illustrated in FIG. 2, all or a portion of makeup quantity of oxygen 14 may be fed to gasifier 105 of gasification zone 100, as oxygen-containing gasifier feed 14a, with an optional portion 14b of this makeup quantity being used in tar conversion operation 110. Oxygen-containing gasifier feed 14a may therefore comprise electrolysis oxygen 19 obtained from electrolyzer 35, and may optionally further comprise ASU oxygen 32 obtained from ASU 45. Oxygen-containing gasifier feed 14a can refer to all gases being fed or added to gasifier 105, whether or not combined upstream of, or within, gasifier 105. For example, oxygen-containing gasifier feed 14a may further comprise other oxygenated gaseous components such as $H_2O$ and/or $CO_2$ that may be combined with electrolysis oxygen 19 and/or ASU oxygen 32 upstream of gasifier 105, or otherwise introduced as a separate $H_2O$— and/or $CO_2$-containing feed 12 to gasification zone 100, or, more particularly, gasifier 105.

As is further illustrated in the more general flowscheme of FIG. 1, in addition to electrolysis oxygen 19, electrolyzer also produces electrolysis hydrogen 18, for example in a makeup quantity that is a stoichiometric amount relative to electrolysis oxygen (e.g., 2 moles of electrolysis hydrogen per mole of electrolysis oxygen), from the electrolysis of added water 30. Electrolysis hydrogen 18 may be combined with at least a portion of gasification zone effluent 16 to provide combined methanation zone feed 20. Alternatively, electrolysis hydrogen 18 may be combined within methanation zone 200, for example with feeds to any of, or any combination of, operations of methanation zone 200, such as those operations shown in the more detailed flowscheme of FIG. 2. According to a preferred embodiment, electrolysis hydrogen 18 is combined with methanation reactor feed 212, or otherwise added directly to methanation reactor 225. Regardless of where electrolysis hydrogen 18 is added to the process (e.g., to the gasification zone 100 or to a feed to any of its constituent operations 105, 110, 115, 120, and/or 125, or to the methanation zone or to a feed to any of its constituent operations 210, 215, 220, and/or 225), electrolysis hydrogen 18 can improve the yield of methane, obtained in methanation reactor effluent 25, by reaction with carbon oxides (CO and/or $CO_2$) that are generated from the gasification of carbonaceous feed 10.

According to FIG. 1, further process integration may be realized by the recovery of gasification zone energy 15 from gasification zone 100 and/or methanation zone energy 17 from methanation zone 200. This energy may be provided to electrolyzer 35, in the form of electrical energy, to meet some or all of the requirements of electrolyzer 35. With reference to FIG. 2, in view of the high temperatures used in gasifier 105, in addition to the highly exothermic reactions occurring in methanation reactor 225, heat may be recovered from products downstream of these operations 105, 225. For example, gasifier heat recovery operation 115 (e.g., comprising a heat exchanger) may be used to recover gasifier heat 118, such as in the form of high pressure steam that is passed to generator 121 that generates gasification zone energy 15 in the form of electricity. Likewise, methanation reactor heat recovery operation 230 (e.g., comprising a heat exchanger) may be used to recover methanation reactor heat 218, such as in the form of high pressure steam that is passed to generator 221 that generates methanation zone energy 17 in the form of electricity. In the embodiment illustrated in FIG. 2, gasifier heat recovery operation 115 recovers heat from hot tar conversion product 106, whereas methanation reactor heat recovery operation 230 recovers heat from hot methanation product 216. Heat, and often low grade heat, may be recovered from the process, for example using gasifier heat recovery operation 115 and/or methanation reactor heat recovery operation 230, for the purpose of pre-heating and/or pre-treating water 30 that is used for electrolysis. Those skilled in the art, having knowledge of the present disclosure, will appreciate that various forms of heat may be recovered and utilized from any of a number of streams of integrated processes described herein. Yet further possibilities for process integration may arise from the recovery of water, for example water that is fed to and/or generated in gasifier 105, from the process. Such water may be more specifically recovered (e.g., condensed) from the effluent of any operation described herein, including from the hot methanation product 216 and/or from the methanation reactor effluent 25 (e.g., as the result of methanation reactor heat recovery operation 230). Recovered water may advantageously provide all or a portion of water 30 that is used for electrolysis, for example in a manner such that external water is not required in the process (i.e., the process is self-sustaining, with respect to water recovery being sufficient to satisfy the water consumption requirement).

FIG. 2 provides a more detailed illustration of the process as illustrated in FIG. 1, but showing operations performed downstream of the gasifier 105 and upstream of the methanation reactor 225, which are namely sequential operations that can be considered as being performed on the gasifier effluent 103, to provide methanation reactor feed 212. Each individual operation can be considered as associated with its respective feed and product streams, in which at least one property (e.g., composition, temperature, and/or pressure) of the product of the operation is changed, relative to the feed to that operation. Also, a product of one operation can be considered as a feed to the next, subsequent operation. The operations may or may not affect, or may or may not substantially affect, the CO and/or $CO_2$ concentration of methanation reactor feed 212 (methanation reactor inlet CO concentration or methanation inlet $CO_2$ concentration), as described above (e.g., they may cause a change (an increase or a decrease) in the absolute concentration, or alternatively the relative amount, of CO and/or $CO_2$ from the inlet of the operation to the outlet of the operation (excluding any flow bypassing the operation) in the ranges as described above). Alternatively, or additionally, the operations may or may not affect, or may or may not substantially affect, the $CO/H_2$ molar ratio and/or $CO_2/H_2$ molar ratio of methanation reactor feed 212 (methanation reactor inlet $CO/H_2$ molar ratio or $CO_2/H_2$ molar ratio), as described above (e.g., they may cause a change (an increase or a decrease) in the absolute molar ratio, or alternatively the relative molar ratio, of $CO/H_2$ and/or $CO_2/H_2$ from the inlet of the operation to the outlet of the operation (excluding any flow bypassing the operation) in the ranges as described above).

In the embodiment of FIG. 2, some operations are shown as being performed in gasification zone 100, whereas others are shown as being performed in methanation zone 200, with the demarcation between these zones 100, 200 being compressor 205 that increases the process pressure from that associated with conditions in gasifier 105 (minus any pressure losses occurring in equipment between gasifier 105 and compressor 205) to that associated with conditions in methanation reactor 225 (plus any pressure losses occurring in equipment between compressor 205 and methanation reactor 225). Therefore, it can be appreciated that, according to some embodiments, operations in gasification zone 100 may be performed at relatively low pressures, for example at an absolute pressure generally from about 0.1 megapascals (MPa) (14.5 psi) to about 3 MPa (435 psi), whereas operations in methanation zone 200 may be performed at relatively high pressures, for example at an absolute pressure from about 2 MPa (290 psi) to about 6.5 MPa (943 psi). However, those skilled in the art, having knowledge of the present disclosure, will recognize that one or more of the operations shown in gasification zone 100 may alternatively be performed in methanation zone 200 and vice versa. Operations may be performed in different orders, relative to the order shown, or otherwise may be excluded. In addition, the depicted operations do not preclude the possibility of one or more additional steps, or operations, occurring upstream and/or downstream of a given illustrated operation, such as reaction (e.g., COS hydrolysis), input or recovery of heat, removal of water, mixing with an auxiliary feed stream, separation of an intermediate product stream (e.g., for $NH_3$ removal), bypassing one or more operations with a portion of a process stream, and/or recycle of a portion of a process stream back to the same operation or an upstream operation.

Representative processes may therefore comprise one or more of the specific operations illustrated in FIG. 2, depending at least partially on the characteristics of carbonaceous feed 10 and conditions in gasifier 105, both of which affect and the composition of gasifier effluent 103 and consequently the subsequent processing operations needed in gasification zone 100 and/or methanation zone 200, for providing a suitable composition of methanation reactor feed 212. In the particular embodiment illustrated in FIG. 2, (i) gasifier effluent 103, which is alternatively a tar conversion feed, is processed in tar conversion operation 110 to provide hot tar conversion product 106, having a reduced concentration of tar; (ii) hot tar conversion product 106, which is alternatively a gasifier heat recovery feed, is cooled in gasifier heat recovery operation 115 to provide gasifier heat recovery product 109, having a lower temperature, in addition to gasifier heat 118, as described above; (iii) gasifier heat recovery product 109, which is alternatively a gas filtration/scrubbing feed, is processed in gas filtration/scrubbing operation 120 to provide gas filtration/scrubbing product 112, having a reduced solid particle content; (iv) gas filtration/scrubbing product 112, which is alternatively a supplemental cleaning feed, is processed in supplemental cleaning operation 125 to provide a supplemental cleaning product, for example as gasification zone effluent 16, as described above, having a reduced concentration of condensable hydrocarbons (e.g., benzene and/or naphthalene); (v) gasification zone effluent 16, which is alternatively a methanation zone feed (or combined methanation zone feed 20, as described above, if combined with at least a portion of electrolysis hydrogen 18), is compressed in compressor 205 to provide compressed product 203, having a higher pressure; (vi) compressed product 203, which is alternatively a sour shift feed, is processed in sour shift operation 210 to provide sour shift product 206, having a higher concentration of $H_2$; (vii) sour shift product 206, which is alternatively a sulfur removal feed, is processed in sulfur removal operation 215 to provide sulfur removal product 209, having a reduced concentration of sulfur compounds (e.g., $H_2S$ and/or COS); and (viii) sulfur removal product 209, which is alternatively an acid gas removal feed, is produced in acid gas removal operation 220 to provide an acid gas removal product, for example as methanation reactor feed 212, as described above, and having a lower concentration of $CO_2$. As described above, methanation reactor feed 212 is processed in methanation reactor 225 to react CO and $CO_2$ with $H_2$ and thereby provide hot methanation product 216, having a higher concentration of methane. Downstream of methanation reactor 225, hot methanation product 216, which is alternatively a methanation reactor heat recovery feed, is cooled in methanation reactor heat recovery operation 230 to provide methanation reactor effluent 25, having a lower temperature, in addition to methanation reactor heat 218, as described above. Hot methanation product 216 and/or methanation reactor effluent 25 may be subjected to drying, and water that is removed in a drying step may be recovered and used, as described above, to provide all or a portion of water 30 for electrolysis.

As illustrated in FIG. 2, electrolysis hydrogen 18, as an exemplary source of makeup hydrogen, may be combined with gasification zone effluent 16, such that only a single compressor 205 may be required for downstream methanation. Alternatively, and as described above, electrolysis hydrogen 18 may be combined with any of compressed product 203, sour shift product 206, sulfur removal product 209, and/or methanation reactor feed 212, for example using a supplemental source of compression (not shown). Combining electrolysis hydrogen 18 with sour shift product 206, for example, may improve the conversion to hydrogen in sour shift operation 210, in view of equilibrium limitations of the WGS reaction. Combining electrolysis hydrogen 18 with either sulfur removal product 209, and/or methanation reactor feed 212 may reduce the overall flows through sulfur removal operation 215 and/or acid gas removal operation 220 and thereby result in lower capital and operating costs due to correspondingly reduced equipment sizes for these operations.

Gasification zone 100 may include one or more gasifiers (e.g., operating in series or parallel), operating under gasifier conditions (e.g., conditions present in a gasification reactor) that include a temperature of generally from about 500° C. (932° F.) to about 1000° C. (1832° F.), and typically from about 750° C. (1382° F.) to about 950° C. (1742° F.). Often, a gasifier is operated with a gasification reactor having a fluidized bed of particles of the carbonaceous feed, with the oxygen-containing gasifier feed, and optionally $H_2O$— and/ or $CO_2$-containing feeds, being fed upwardly through the particle bed. Other gasification reactor configurations include counter-current fixed bed ("up draft"), co-current fixed bed ("down draft"), and entrained flow plasma. Gasifier conditions may also include atmospheric pressure or elevated pressure, for example an absolute pressure generally from about 0.1 megapascals (MPa) (14.5 psi) to about 10 MPa (1450 psi), and typically from about 1 MPa (145 psi) to about 3 MPa (435 psi). Various catalytic materials may be used in a gasification reactor, including solid particles of dolomite, supported nickel, alkali metals, and alkali metal compounds such as alkali metal carbonates, bicarbonates, and hydroxides. Different catalysts, having differing activities for one or more desired functions in gasification, such as tar reduction, enhanced $H_2$ yield, and/or reduced $CO_2$ yield, may be used. Limestone may be added to a gasification reactor, for example, to promote tar reduction by cracking. The gasifier effluent, which may also be referred to as syngas, generally contains CO, $CO_2$, $H_2$, water, methane, sulfur compounds (e.g., $H_2S$ and/or COS), nitrogen compounds (e.g., $NH_3$), tar, and solid particulates. According to representative embodiments, the gasifier effluent $H_2$ concentration is generally from about 10 mol-% to about 55 mol-%, and typically from about 20 mol-% to about 45 mol-%. The CO and $CO_2$ concentrations are each generally from about 5 mol-% to about 50 mol-%, and typically from about 15 mol-% to about 35 mol-%. The methane concentration is generally from about 1 mol-% to about 15 mol-%, and typically from about 2 mol-% to about 10 mol-%. The gasifier effluent may comprise mainly (e.g., in a combined concentration of at least about 75 mol-%, at least about 80 mol-%, or at least about 85 mol-%) the components CO, $CO_2$, water, and $H_2$.

Tar conversion operation 110 may be used to reduce the concentration of tar (organic compounds having a boiling point temperature greater than that of benzene) in the gasifier effluent, produced by the gasification. Compounds removed by tar conversion, or tar reforming, include $C_6^+$ hydrocarbons (e.g., toluene and/or naphthalene) and oxygenates such as phenol. In the absence of tar conversion, the amount of tar produced by biomass gasification can be sufficient, over time, to cause serious problems in downstream equipment such as corrosion and/or plugging. The tar conversion operation may include a separate reactor, containing a bed of catalyst comprising solid or supported Ni, solid or supported Fe, and/or dolomite, for example in the form of a secondary fluidized bed downstream of a gasifier. Other catalysts for tar conversion include olivine, limestone, zeolites, and even metal-containing char produced from the gasification. Tar may alternatively be converted by non-catalytic partial oxidation. According to one embodiment, tar may be converted by both cracking and steam reforming to beneficially increase the yield of $H_2$ and $CO_2$, initially obtained from gasification, often while maintaining the yield of methane, initially obtained. Tar conversion reactions may be performed at temperatures higher than those used in the gasifier, such as above 1000° C. (e.g., from about 1000° C. (1832° F.) to about 1250° C. (2282° F.)).

Gas filtration/Scrubbing operation 120 may be used to remove solid particles (particulates) in a gasifier effluent. In the case of biomass gasification, the solid particles formed include char, tar, soot, and ash, any of which can generally contain alkali metals such as sodium. Corrosive and/or harmful species such as chlorides, arsenic, and/or mercury may also be contained in such particulates. A high temperature filtration, for example using bundles of metal or ceramic filters, may generally be sufficient to reduce the content of particulates in the gasifier effluent to less than 1 wt-ppm, and possibly less than 0.1 wt-ppm. In some embodiments, gas filtration/scrubbing operation 120 may be performed upstream of (prior to) tar conversion operation 110 to allow the latter to operate more effectively.

Supplemental cleaning operation 125 may be used to further reduce the tar and overall hydrocarbon content of a gasifier effluent, for example by contact with a solid "polishing" material such as a carbon bed. This can provide for more thorough removal of benzene, naphthalene, toluene, phenols, and other condensable species that could otherwise be detrimental to the operation of compressor 205 and/or could deposit onto, and thereby cause deactivation of, catalyst used in the methanation reactor (e.g., by blockage of catalytically active Ni sites of the catalyst).

Sour shift operation 210 may be used to perform a WGS reaction, in the presence of sulfur compounds, and thereby increase the concentration of $H_2$ (or the $H_2$:CO molar ratio) relative to that initially in a gasifier effluent, as obtained from a gasifier. This operation may include one or more WGS reactors (e.g., operating in series or parallel) having a suitable catalyst that is resistant to deactivation in the presence of $H_2S$ and/or COS, such as a cobalt-molybdenum catalyst. Other catalysts for this purpose include those based on copper-containing and/or zinc-containing catalysts, such as Cu—Zn—Al; chromium-containing catalysts; iron oxides; zinc ferrite; magnetite; chromium oxides; and any combination thereof (e.g., $Fe_2O_3$—$Cr_2O_3$ catalysts). Conditions for the catalytic WGS reaction include a temperature from about 150° C. (302° F.) to about 400° C. (752° C.).

Sulfur removal operation 215 may be used to reduce the concentration of sulfur compounds, including $H_2S$, COS, and/or $SO_2$, in a gasifier effluent. These compounds, which result from the presence of trace quantities of sulfur in carbonaceous feeds, including biomass, may be detrimental to (e.g., poison) catalyst used in a methanation reactor, for example due to the formation of nickel sulfide at catalytically active Ni sites of the catalyst. The sulfur removal operation may include contacting the gasifier effluent at any stage of the process (e.g., downstream of a sour shift operation as shown in FIG. 2) with a guard bed suitable to obtain a product that is essentially free of sulfur, for example having less than 1 wt-ppm, such as less than 0.1 wt-ppm, of total sulfur. Suitable guard bed materials include those used in water treatment, such as iron-containing sorbent (iron "sponge") materials and/or zinc oxide.

Acid gas removal operation 220 may be used to reduce the concentration of $CO_2$ and/or other acid gases (e.g., $H_2S$) relative to the respective concentrations initially in a gasifier effluent, as obtained from a gasifier, and/or relative to the respective concentrations obtained in a sour shift product. The acid gas removal operation may utilize one or more stages of contacting with a physical solvent such as Selexol® (dimethyl ethers of polyethylene glycol), Rectisol® (cold methanol), or a combination thereof. One or more amine solvents such as monoethanolamine, diethanolamine, methyldiethanolamine, diisopropylamine, or diglycolamine, or otherwise methanol, potassium carbonate, a solution of sodium salts of amino acids, etc. can also be used to remove at least a portion of an acid gas. An acid gas removal product, upstream of a methanation reactor, may have a $CO_2$ concentration generally from about 2 mol-% to about 40 mol-%, and typically from about 5 mol-% to about 20 mol-%, and may have a total sulfur concentration of less than about 0.1 mol-ppm.

Methanation zone 200 may include one or more methanation reactors (e.g., operating in series or parallel) to react CO and/or CO$_2$ with hydrogen and thereby provide a hot methanation product, and/or ultimately a methanation reactor effluent, having a significantly higher concentration of methane, relative to that initially in a gasifier effluent, as obtained from a gasifier. Catalysts suitable for use in a methanation reactor include supported metals such as ruthenium and/or other noble metals, as well as molybdenum and tungsten. Generally, however, supported nickel catalysts are most cost effective. Often, a methanation reactor is operated using a fixed bed of the catalyst. Other conditions suitable for a methanation reactor include a temperature of generally from about 250° C. (482° F.) to about 600° C. (1112° F.), and typically from about 350° C. (662° F.) to about 500° C. (932° F.). Methanation conditions may also include an absolute pressure generally from about 1.4 (MPa) (203 psi) to about 6.9 MPa (1000 psi), and typically from about 2.8 MPa (406 psi) to about 5.5 MPa (798 psi). The concentration of methane in a methanation reactor effluent (e.g., an RNG product), or a product recovered from this effluent, may be generally at least about 60 mol-% (e.g., from about 60 mol-% to about 99.9 mol-%), and typically at least about 80 mol-% (e.g., from about 80 mol-% to about 99 mol-%). Such effluents and/or products may have other properties of "pipeline quality" methane, as described above.

Overall, aspects of the invention relate to improvements in the utilization of hydrogen, for example electrolysis hydrogen as a makeup source that is supplied in conjunction with a stoichiometric amount of electrolysis oxygen to integrated gasification and methanation processes, for the production of methane. Those skilled in the art, having knowledge of the present disclosure, will recognize that various changes can be made to these processes in attaining these and other advantages, without departing from the scope of the present disclosure. As such, it should be understood that the features of the disclosure are susceptible to modifications and/or substitutions, and the specific embodiments illustrated and described herein are for illustrative purposes only, and not limiting of the invention as set forth in the appended claims.

The invention claimed is:

1. A process for producing methane, the process comprising:
   in a gasifier, contacting a carbonaceous feed with an oxygen-containing gasifier feed to provide a gasifier effluent comprising CO, CO$_2$ and H$_2$;
   in a methanation reactor, reacting electrolysis hydrogen, obtained from an electrolyzer, with at least a portion of the CO and/or CO$_2$ in the gasifier effluent to form methane, and
   adjusting an operation of the process, affecting a methanation reactor inlet CO concentration or a methanation reactor inlet CO$_2$ concentration, in response to a makeup quantity of the electrolysis hydrogen,
   wherein the operation is upstream of the methanation reactor and not a recycle of a portion of a process stream back to an upstream operation.

2. The process of claim 1, further comprising obtaining a methane product as, or recovering the methane product from, the methanation reactor effluent.

3. The process of claim 1, wherein the operation of the process, affecting the methanation reactor inlet CO concentration or the methanation reactor inlet CO$_2$ concentration, (i) consumes or produces CO or CO$_2$ in the process, or (ii) adds or removes CO or CO$_2$ in the process.

4. The process of claim 3, wherein the operation of the process, affecting the methanation reactor inlet CO concentration or the methanation reactor inlet CO$_2$ concentration, is a sour shift operation that consumes CO and produces CO$_2$ in the process, or an acid gas removal operation that removes CO and CO$_2$ in the process.

5. The process of claim 1, wherein the operation is adjusted by bypassing at least a portion of a feed to the operation.

6. The process of claim 1, wherein the operation is adjusted to obtain a methanation reactor inlet ratio of $[H_2]/(3 \cdot [CO]+4 \cdot [CO_2])$ from about 0.7 to about 1.5.

7. The process of claim 1, wherein the carbonaceous feed comprises coal or biomass.

8. The process of claim 1, wherein the oxygen-containing gasifier feed comprises electrolysis oxygen, obtained from the electrolyzer.

9. The process of claim 8, wherein the oxygen-containing gasifier feed further comprises ASU oxygen obtained from an air separation unit.

10. The process of claim 9, wherein the electrolysis oxygen and the ASU oxygen provide a makeup quantity of oxygen that is determined at least partly on the basis of a makeup quantity of the carbonaceous feed.

11. The process of claim 1, wherein the oxygen-containing gasifier feed further comprises H$_2$O and/or CO$_2$.

12. The process of claim 1, further comprising one or more additional operations, downstream of the gasifier and upstream of the methanation reactor, the one or more additional operations performing respective one or more processing steps on the gasifier effluent, the processing steps selected from the group consisting of converting tar, recovering heat, filtering/scrubbing, supplemental cleaning, and removing sulfur.

13. An integrated gasification, methanation, and electrolysis process for producing renewable natural gas, the process comprising:
   in a gasifier of a gasification zone, contacting biomass with an oxygen-containing gasifier feed to provide a gasification zone effluent comprising CO, CO$_2$ and H$_2$, wherein the oxygen-containing gasifier feed comprises electrolysis oxygen obtained from electrolysis of water in an electrolyzer;
   in a methanation reactor of a methanation zone, converting at least a portion of the CO and/or the CO$_2$ in the gasification zone effluent to methane; and
   obtaining the renewable natural gas as, or recovering the renewable natural gas from, a methanation zone effluent,
   wherein the gasification zone or the methanation zone comprises at least one operation affecting CO concentration or CO$_2$ concentration, the process further comprising adjusting the operation in response to a makeup quantity of electrolysis hydrogen obtained from the electrolyzer, and
   wherein the operation is upstream of the methanation reactor and not a recycle of a portion of a process stream back to an upstream operation.

14. The process of claim 13, wherein the gasification zone comprises, in addition to the gasifier, one or more operations selected from the group consisting of a tar conversion operation, a gasifier heat recovery operation, a gas filtration/scrubbing operation, and a supplemental cleaning operation.

15. The process of claim 13, wherein the methanation zone comprises, in addition to the methanation reactor, one or more operations selected from the group consisting of a sour shift operation, a sulfur removal operation, an acid gas removal operation, and a methanation reactor heat recovery operation.

16. The process of claim 15, wherein the at least one operation affecting CO concentration or $CO_2$ concentration is the sour shift operation or the acid gas removal operation.

17. The process of claim 13, further comprising combining at least a portion of the gasification zone effluent with electrolysis hydrogen obtained from the electrolyzer, for reaction in the methanation zone to provide at least a portion of the methane in the methanation zone effluent.

18. The process of claim 17, wherein the electrolysis hydrogen increases the yield of methane based on carbon present in the biomass, by at least about 10% relative to a baseline process performed without addition of the electrolysis hydrogen.

19. The process of claim 13, wherein the renewable natural gas obtained as, or recovered from, the methanation zone effluent, is pipeline quality natural gas.

20. A process for producing methane, the process comprising:
    gasifying a carbonaceous feed to provide a gasifier effluent comprising CO, $CO_2$ and $H_2$;
    introducing a makeup quantity of hydrogen to the methanation reactor or upstream of the methanation reactor, to react at least a portion of the makeup hydrogen with at least a portion of the CO and/or $CO_2$ in the gasifier effluent to form methane, and
    adjusting an operation of the process in response to the makeup quantity of hydrogen,
    wherein the operation is upstream of the methanation reactor, and further wherein the operation is not a recycle of a portion of a process stream back to an upstream operation.

21. The process of claim 20, wherein the process excludes at least one processing step on the gasifier effluent of sour shifting or removing acid gas.

22. A process for gasification of a carbonaceous feed, the process comprising:
    in a gasifier, contacting the carbonaceous feed with an oxygen-containing gasifier feed, performing a series of operations downstream of the gasifier to provide a gasifier effluent comprising CO, $CO_2$ and $H_2$, wherein at least one of said series of operations causes a change in a concentration of CO and/or $CO_2$ from an inlet of said at least one operation to an outlet of said at least one operation, or otherwise causes a change in a relative amount of CO and/or $CO_2$ from the inlet of said at least one operation to the outlet of said at least one operation,
    the process further comprising:
    adjusting said at least one of said series of operations, in response to a makeup quantity of electrolysis hydrogen, said makeup quantity being provided by an electrolyzer that further provides a makeup quantity of oxygen for said oxygen-containing gasifier feed,
    wherein said adjusting is performed to maintain a $CO/H_2$ molar ratio of the gasifier effluent, following combining of said makeup quantity of electrolysis hydrogen with a product of any of said series of operations.

23. The process of claim 22, wherein said makeup quantity of oxygen is determined based on both a makeup quantity of the carbonaceous feed and a characteristic of the carbonaceous feed.

24. The process of claim 23, wherein the characteristic is a carbon content of the carbonaceous feed.

25. The process of claim 22, wherein said at least one operation of the process is a sour shift operation that consumes CO and produces $CO_2$ in the process, or an acid gas removal operation that removes CO and $CO_2$ in the process.

26. The process of claim 22, wherein said at least one operation is adjusted by bypassing at least a portion of a feed to the operation.

27. The process of claim 22, wherein said series of operations perform one or more of converting tar, recovering heat, filtering/scrubbing, supplemental cleaning, and removing sulfur, to provide said gasifier effluent.

* * * * *